United States Patent
Williams, III

(10) Patent No.: US 7,498,018 B2
(45) Date of Patent: Mar. 3, 2009

(54) CONTRAST MEDIA FOR USE IN MEDICAL AND DIAGNOSTIC PROCEDURES AND METHODS OF USING THE SAME

(75) Inventor: Archie B. Williams, III, Smithtown, NY (US)

(73) Assignee: Bracco Diagnostics Inc., Princeton, NJ (US)

( * ) Notice: Subject to any disclaimer, the term of this patent is extended or adjusted under 35 U.S.C. 154(b) by 637 days.

(21) Appl. No.: 10/679,052

(22) Filed: Oct. 3, 2003

(65) Prior Publication Data

US 2005/0074405 A1  Apr. 7, 2005

(51) Int. Cl.
A61K 49/04 (2006.01)
A61K 49/00 (2006.01)

(52) U.S. Cl. .................. 424/9.4; 424/9.1; 424/9.411

(58) Field of Classification Search ............... 424/9.41, 424/9.4, 9.411
See application file for complete search history.

(56) References Cited

U.S. PATENT DOCUMENTS

| | | | |
|---|---|---|---|
| 4,588,574 A | 5/1986 | Felder et al. | 424/9.41 |
| 5,160,724 A | 11/1992 | Tonariya et al. | 424/9.411 |
| 5,242,455 A | 9/1993 | Skeens et al. | 606/130 |
| 5,518,711 A | 5/1996 | Tonariya et al. | 424/9.411 |
| 5,550,263 A | 8/1996 | Herslof et al. | |
| 5,611,342 A * | 3/1997 | Widder | 600/431 |
| 5,702,682 A | 12/1997 | Thompson | 424/9.42 |
| 5,741,477 A | 4/1998 | Davis et al. | 424/9.31 |
| 5,920,319 A | 7/1999 | Vining et al. | 345/420 |
| 6,001,334 A | 12/1999 | Hirai | 424/9.411 |
| 6,125,295 A | 9/2000 | Cash, Jr. et al. | 600/431 |
| 6,272,366 B1 | 8/2001 | Vining | 600/407 |
| 6,477,401 B1 * | 11/2002 | Johnson et al. | 600/431 |
| 2001/0036442 A1 * | 11/2001 | Tait | 424/9.41 |
| 2005/0175542 A1 * | 8/2005 | Lefere et al. | 424/9.41 |

FOREIGN PATENT DOCUMENTS

DE  23830  * 8/1986

JP  08-169849  * 7/1996

OTHER PUBLICATIONS

Ramm, U. et al., Phys. Med. Biol., 2001, 46, p. 2631-2635.*
Nyman, U. et al., Acta Radiol. Diagn., 1984, 25, p. 121-124.*
Zeman, R., et al., Am. J. Roentgenology, 1998, 170, p. 1427-1438.*
Gore, R., et al., Am. J. Roentgenology, 1984, 143, p. 279-284.*
Balthazar, E., et al., Am. J. Roentgenology, 988, 150, p. 301-306.*
Ha, H., et al., Radiology, 1998, 209, p. 449-454.*
Litt et al., Acad. Radiol, 2001, 8, p. 377-383.*
Raptopoulos et al., Radiology, 1987, 164, p. 653-656.*
Applied Radiology—MR imaging of the gastrointestinal tract and the peritoneum; Russell N. Low, MD, Aug. 2003; www.appliedradiology.com.
Center for Drug Evaluation and Research; Application No. NDA 20773; Final Printed Labeling Academic Radiology, vol. 10, No. 5, May 2003; Evaluation of Simethicone-coated Cellulose as a Negative Oral Contrast Agent for Abdominal Ct.
Academic Radiology, vol. 9, Suppl 2, 2002; Evaluation of Simethicone Coasted Celllulose (SonoRx™ as a Negative Oral Contrast Agent for Abdominal-pelvic Computed Tomography.
Dizendorf et al., "Cause and Magnitude of the Error Induced by Oral CT Contrast Agent in CT-Based Attenuation Correction of PET Emission Studies," *The Journal of Nuclear Medicine*, vol. 44, No. 5, May 2003, pp. 732-738.
Sosna et al., "Colorectal Neoplasms: Role of Intravenous Contrast-enhanced CT Colonography," *Radiology*, vol. 228, No. 1, Jul. 2003, pp. 152-156.

* cited by examiner

*Primary Examiner*—Michael G Hartley
*Assistant Examiner*—Leah Schlientz
(74) *Attorney, Agent, or Firm*—Alston & Bird LLP

(57) ABSTRACT

The present invention relates to contrast media having a low concentration of contrast agent (active ingredient) and/or low Hounsfield value for use in medical or diagnostic procedures, or for therapeutic use. In one alternative embodiment, the contrast media are comprised of a contrast agent, alone or in combination with a stabilizing agent or osmotic agent. The present invention is directed to a contrast media having a Hounsfield value less than 250. In another embodiment, the contrast media comprises a contrast agent, such as a less than 2% w/v barium-based compound. In another embodiment, the present invention also relates to formulations and methods for distending and imaging an anatomic segment of an individual.

65 Claims, 6 Drawing Sheets

CONTRAST MEDIA FOR USE IN MEDICAL AND DIAGNOSTIC PROCEDURES AND METHODS OF USING THE SAME

I. FIELD OF THE INVENTION

The present invention relates to formulations having low concentrations of contrast agent and/or low Hounsfield values for use in a medical or diagnostic procedure such as imaging or surgery, or for therapeutic use. The present invention also relates to methods for distending or imaging an anatomic segment using the formulations of the present invention. In one alternative embodiment, the formulations of the present invention are especially suitable for use with diagnostic imaging procedures, including, but not limited to, magnetic resonance imaging (MR), computed tomography (CT), ultrasound (US), position emission tomography (PET), and combined modalities such as CT-PET, as well as other medical and therapeutic uses.

II. BACKGROUND OF THE INVENTION

Contrast agents are useful in diagnostic imaging because they make it possible to determine the location, size and identity of organs or other structures of the body in the context of their surrounding tissues. In the early days of radiographic contrast development, researchers realized the value of an element's density for use as a contrast agent. Barium-based compounds, particularly BaSO4, soon became the preferred contrast agent due to its high atomic weight and its low cost to produce. In addition, its safety profile reinforced this direction of development.

In time, fluoroscopic imaging enabled radiologists to monitor contrast agents as they moved through the GI tract. This advancement required individual BaSO4 suspensions for each segment of the GI tract. Based on the portion of the GI tract being imaged, different contrast media comprising barium sulfate were developed. For the esophagus, a thick paste was used to show esophageal motility and outline the myocardium (heart) and great vessels (aorta) of the thorax. These pastes were high in concentrations of barium sulfate (100% w/v). To study the stomach, a media concentration of barium sulfate (40-80% w/v) was used. In the small bowel, concentrations usually were the same or slightly less as those used for the stomach. Single contrast studies of the colon were performed by rectal administration. Here, sulfate concentrations of 15-18% w/v were used to fill and distend the colon and distal small bowel. In the 1960's and 1970's, double contrast or air contrast studies were performed on both the upper and lower GI. In these studies, the barium sulfate concentrations for the upper and lower GI were 250% w/v and 100% w/v, respectively.

In the development of computerized axial tomography ("CAT" or "CT"), radiologists used orally administered barium sulfate or dilute iodine solutions to distinguish bowel from other surrounding tissue. Due to the sensitivity of CT, lower concentrations of BaSO4 (2.1% w/v) could be used, as well as dilute iodine solutions.

The introduction of multi-detector helical scanners provided improved quality and image definition. With helical scanner, the current 2.1% barium sulfate concentrations can be used to differentiate the GI tract from the surrounding tissue, but do not allow clear differentiation between bowel wall and bowel lumen. When conventional bowel markers are used the adjacent soft tissues are lost in the image acquisition phase. This is due to a phenomena known as volume averaging. When the radiopaque contrast materials conventionally used are in the bowel lumen, the soft tissue of the bowel wall is lost in the image reconstruction.

The lower contrast media concentrations of the present formulations, when used with, for example, spiral, helical and multi-detector helical scanners (MSMD) in CT and in MR, allows for lumen distention and clear visualization of organs and other structures, for example:

In CT, the newer imaging technology allows for improved image quality and allows image detail of minor HV differences to be appreciated. The conventional oral bowel markers do not allow imagers to take advantage of the bowel marking and imaging of adjacent soft issues. With the older/higher concentration used in conventional CT, the bowel wall is not visualized. The soft tissue next to the dense contrast marking the bowel lumen will cause loss of imaging ability of the adjacent (soft tissue) bowel wall. Much like the penumbra when light passes through space spreading out and including adjacent space. reconstruction of high densities in CT casts a shadow on contiguous low density soft tissue structures called "volume averaging." This concept may be analogized in terms of the CT image being comprised of pixels. Each pixel has a value based on the anatomy it represents if it is bright then it is dense and has a high HV. When you have pixels lined up in a row, as we have in every CT image, there are dense pixels and less dense pixels. When these adjacent pixels have great differences in HV's, like we would expect to see in the GI tract bowel wall (45 HV) and the lumen with conventional CT contrast (250 to 450 HV), there is an averaging effect. The pixels of lower density values of the bowel wall are increased and the bowel lumen contrast of higher density pixels are slightly decreased. The net effect is the loss of bowel wall in the image.

There is, therefore, a need for a contrast media having a lower Hounsfield value and/or lower concentration of contrast agent to effectuate high quality imaging of organs or other structures in a medical or diagnostic procedure, or for therapeutic use.

III. SUMMARY OF THE INVENTION

The present invention relates to contrast media formulations having a low concentration of contrast agent and/or low Hounsfield value for use in medical or diagnostic procedures, or for therapeutic use. In one alternative embodiment, the contrast media is comprised of a contrast agent, alone or in combination with a stabilizing agent or osmotic agent. In one embodiment, the present invention is directed to a contrast media having a Hounsfield value less than 250 and preferably less than 100. In another embodiment, the contrast media comprises a contrast agent, such as a barium-based compound. In yet another embodiment, the present invention also relates to formulations and methods for bowel marking, bowel distention and imaging of an anatomic bowel segment of an individual. Additionally, the formulations of the present invention are especially suitable for use with diagnostic imaging procedures including, but not limited to, fluoroscopy (X-Ray), magnetic resonance imaging (MR), computed tomography (CT), CT-PET (position emission tomography and ultrasound (US), as well as other medical and therapeutic uses.

IV. DESCRIPTION OF THE FIGURES

V. DETAILED DESCRIPTION OF THE INVENTION

Figure 1:
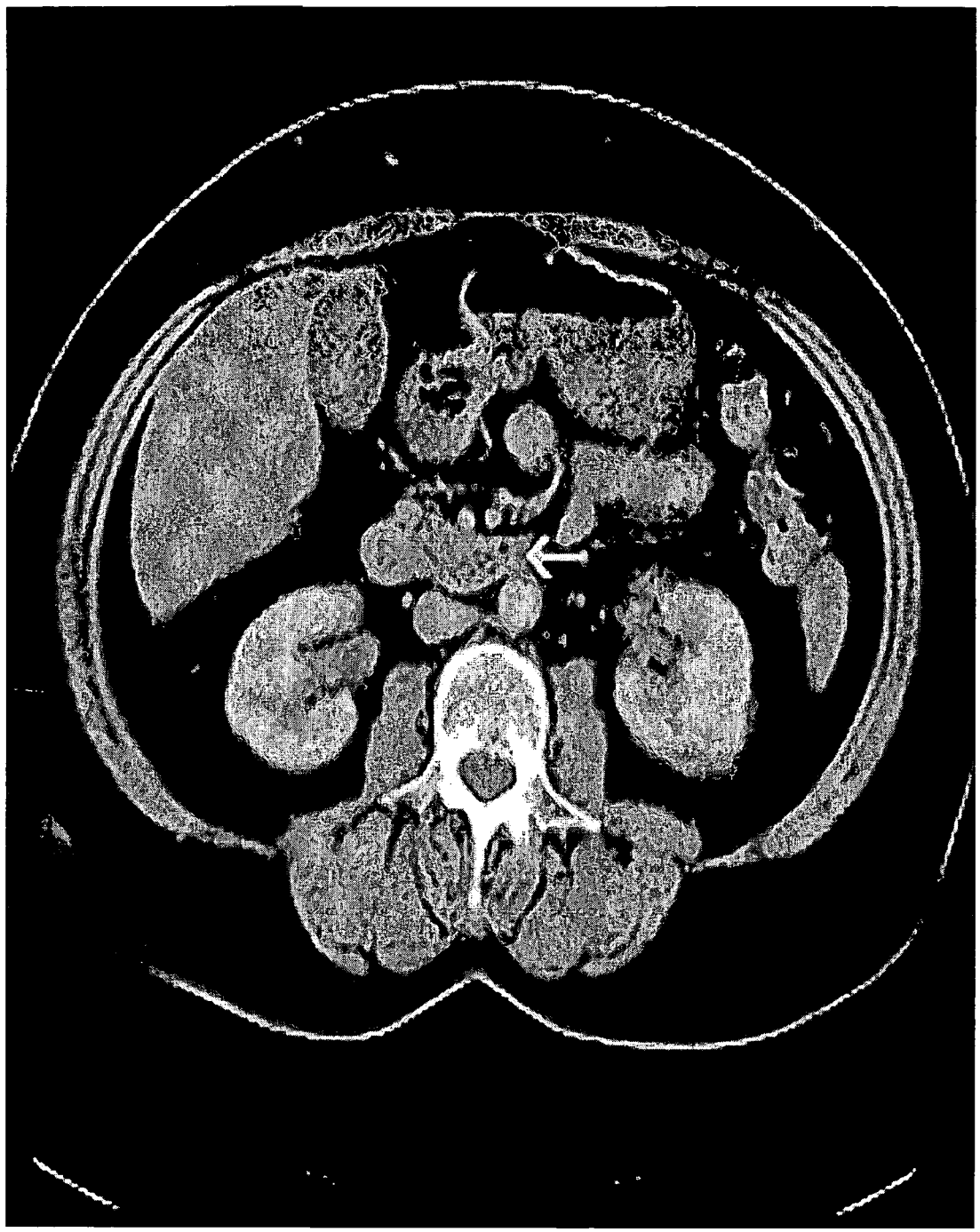
FIG. 1 shows CT image of an abdomen of an individual administered the present invention.

The present invention is directed to contrast media suitable for use in a medical or diagnostic procedure such as diagnostic imaging. Diagnostic imaging techniques suitable for use herein include, but are not limited to, X-ray imaging, MR, CT, US, optical imaging, SPECT, PET, flat-panel imaging, and using rigid, flexible or capsule endoscopy. A combination of CT and PET imaging, namely, CT-PET is also suitable for use with the present invention. Preferably, the diagnostic imaging technique used herein is MR, CT, CT-PET or US.

The present contrast formulations may be useful in diagnostic imaging of any anatomic structure of the body. In one embodiment, the present invention is especially suited for use in diagnostic imaging of anatomic segments including, but not limited to, the esophagus, the stomach and GI tract, including the duodenum, small bowel (jejunum, ileum, appendix and cecum) and the large intestine, (ascending bowel, hepatic flexure, transverse colon, splenic flexure, descending colon, sigmoid and rectum). Additionally, the present invention is particularly suited for imaging tissues and organs such as the pancreas, gall bladder, spleen, liver, lymph nodes, and the vasculature, as well as pathologic entities such as abscesses and the like.

A. Formulation

More particularly, the present invention relates to contrast media formulation having a low Hounsfield value (HV), including a positive or negative HV. In one embodiment, the present invention relates to contrast media for diagnostic imaging comprising low concentrations of contrast agent, alone or in combination with a stabilizing agent or an osmotic agent.

1. Contrast Agent

The contrast media of the present invention include any composition of matter that can, upon administration to an individual, affect a lumen or tissue (e.g. fill, distend, label and/or mark) so that an area of interest can be differentiated from surrounding tissue during a medical activity, for example. Such medical activities including, but not limited to, a diagnostic, surgical or therapeutic procedure.

Contrast media of the present invention may comprise one or more contrast agents, including but not limited to, barium-based compounds, such as barium sulfate, organically-bound iodine-based compounds of both the non-ionic and ionic type or any combination of the above mentioned compounds. Other agents may include gadolinium-based compounds (or any other metallic elements used in MR imaging, including, but not limited to, Fe, Dy, Mn), stabilizing agents, bentonite-based compounds or any other suitable inert or insoluble compounds, including but not limited to, metallic oxides/silicates/sulfates/hydroxides such as milk of magnesia fat-based compounds, lipids or triglycerides, or any combination the of the above-mentioned compounds.

In the present invention, doses of contrast agent may be administered via many different dosage forms. The contrast media may take many forms including but not limited to, liquid, suspension, paste, powder, concentrate, granulated powder for mixing to proper concentration or solid form. For example, the contrast media may be consumed as a drink, it may also be administered orally by other means or administered rectally. In addition the oral or rectal route, the contrast media may be administered percutaneously or via intubation. Also, the contrast media may be consumed as a suspension or swallowed as a tablet, capsule or caplet.

In another alternative embodiment, the total amount of contrast agent (active ingredient) administered to the individual prior to or during the medical activity may be at least about 0.01 g, 0.025 g, 0.05 g, 0.075 g, 0.1 g, 0.5 g, 1 g, 5 g, 10 g, 20 g, 30 g, 50 g, 70 g, 10 g, 120 g, 150 g, 180 g, 200 g, 300 g, 350 g, 400 g, 450 g, 500 g, 550 g, 600 g or more. The preferred range is from about 1 g to about 3 g, more preferably about 2 g to about 2.5 g.

The contrast agent may be provided in a contrast media having a volume of about 10 ml to about 10 L, or about 100 ml to about 5 L, or about 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 1 L, 1.5 L, 2 L, 2.5 L, 3 L, 3.5 L, 4 L or 4.5 L.

The contrast media may be administered in single dosage, or may be divided into multiple dosages. For example, if the contrast media is 2 L, then the patient may consume 1 L about 2 hours prior to the procedure, and the remaining 1 L about 1 hour prior to the procedure. Another approach is to have the patient consume 150 ml every 5 minutes until the total volume required for specific procedure is consumed.

2. Concentration of Contrast Agents

In one alternative embodiment, the contrast media of the present invention may comprise any appropriate amount of contrast agent, provided that the value of the contrast media comprising the contrast agent, alone or with other excipients, is less than 250 HV.

In one alternative embodiment, the contrast media of the present invention may comprise less than 1% by weight of a barium-based compound. In another alternative embodiment, the present invention may comprise from about 0.001% to about 0.8% barium-based compound, preferably from about 0.01% to about 0.5%, more preferably about 0.1% or about 0.5%. Other concentrations of barium-based compound that may be suitable in the present invention include 0.02%, 0.03%, 0.04%, 0.06%, 0.07%, 0.08%, 0.09%, 0.11%, 0.15%, 0.20%, 0.25%, 0.30%, 0.35%, 0.40%, 0.45%, 0.50%, 0.55%, 0.60%, 0.65%, 0.70%, 0.75%, 0.80%, 0.90%, or 0.95% by weight. The preferred barium-based compound is barium sulfate.

In one alternative embodiment, the contrast media of the present invention may comprise less than 1% by weight of a contrast agent. In another alternative embodiment, the present invention may comprise from about 0.001% to about 0.8% iodine based compound, preferably from about 0.01% to about 0.5%, more preferably about 0.1% or about 0.05%, most preferably, about 0.1% iodine based compound. Other concentrations of iodine based compound that may be suitable in the present invention include 0.02%, 0.03%, 0.04%, 0.06%, 0.07%, 0.08%, 0.09%, 0.11%, 0.15%, 0.02%, 0.25%, 0.30%, 0.35%, 0.40%, 0.45%, 0.50%, 0.55%, 0.60%, 0.65%, 0.70%, 0.75%, 0.80%, 0.90%, or 0.95% by weight.

In one alternative embodiment, the contrast media of the present invention may comprise less than 1% by weight of a contrast agent. In another alternative embodiment, the present invention may comprise from about 0.001% to about 0.8% gadolinium based compound, preferably from about 0.01% to about 0.5%, more preferably about 0.1% or about 0.05%, most preferably, about 0.1% gadolinium based compound. Other concentrations of gadolinium based compound that may be suitable in the present invention include 0.02%, 0.03%, 0.04%, 0.06%, 0.07%, 0.08%, 0.09%, 0.11%, 0.15%, 0.20%, 0.25%, 0.30%, 0.35%, 0.40%, 0.45%, 0.50%, 0.55%, 0.60%, 0.65%, 0.70%, 0.75%, 0.80%, 0.90%, or 0.95% by weight.

3. Hounsfield Value of Contrast Media

The HV of the contrast media may be determined by CT using procedures well known in the art. As used herein, Hounsfield units or Hounsfield values ("HV") are units of X-ray attenuation used for CT scans. Each pixel being assigned a value on a scale where air=−1000, water=0, and compact bone=1000. In the present invention, the HV of the contrast media (with excipients, if any) may be determined by placing it in an HDPE container and placing the container in a CT scanner (e.g., Siemens 4 channel scanner) to determine the HV of the formulation. The container may comprise any known HDPE used in the medical industry for packaging non-radioactive oral contrast agents for CT.

Example of apparatuses suitable for practicing the present invention include, but are not limited to, spiral/helical CT scanners with multi-detector/multi-slice capabilities. Other apparatuses include, but are not limited to, GE: CT: LightSpeed Series and HiSpeed MR: Signa Excite Series CT/PET: Discovery Series Philips: CT: Mx8000 Series MR: Intera Series CT/PET: Gemini Siemens: CT: Somatom MRT: Magnetom CT/PET: biograph Toshiba: CT; Aquilion Steion Multi MR: Ultra, Excelart and flat panel (which. will allow for large volumes of data to be acquired over large area instantaneously).

In one alternative embodiment, the contrast media of the present invention comprise a contrast agent having an HV value from about −500 to about 250. In another embodiment, the HV value may range from about −100 to about 100, preferably from about 15 to 35, more preferably from about 20 to 30. In another embodiment, the HV value may range from −500 to 0 HV, more preferably less than 0. The lower range may differentiate the lumen of the GI from surrounding organs when the GI tract is distended with the present invention.

Other suitable HV ranges include from about: −500 to 400; −400 to −300; −300 to 200; −200 to 100; −100 to 0; 0 to 5; 5 to 10; 10 to 15; 15 to 20; 20 to 25; 25 to 30; 30 to 35; 35 to 40; 40 to 45; 45 to 50; 55 to 60; 60 to 65; 65 to 70; 75 to 80; 80 to 85; 85 to 90; 90 to 95; 95 to 100; 100 to 110; 110 to 120; 130 to 140; 140 to 150; 150 to 160; 160 to 170; 170 to 180; 180 to 190; 190 to 200; 210 to 220; 220 to 230; 240 to 250.

4. Stabilizing Agent

In one alternative embodiment, the contrast media of the present invention comprises a stabilizing agent. Such agent may include any compound (e.g. suspending agent) that modifies the viscosity of a substance, including any fluid, semi-fluid or solid. Stabilizing agents suitable for use herein may include, but are not limited to, cellulose, gelatin, natural hydrocolloids, bentonite, locust bean gum or any compound that appropriately modifies the viscosity of a substance so as to facilitate the imaging process.

Natural hydrocolloids suitable for use in the present formulations include, but are not limited to, (1) natural seaweed extracts such as carrageenan, alginates, agar, agarose, fucellan and xanthan gum; (2) natural seed gums such as guar gum, locust bean gum, tara gum, tamarind gum and psillium gum; (3) natural plant exudates acacia, tragacanth, karaya and ghatti gums; (4) natural fruit extracts such as low and high methoxyl pectins; (5) natural and purified clays such as bentonite and veegum to alter viscosity and lower signal/noise ratios to improve performance in MR imaging.

In one alternative embodiment, the stabilizing agent is a natural seed gum, and, even more preferably, locust bean gum. The chemical structure of locust bean gum is:

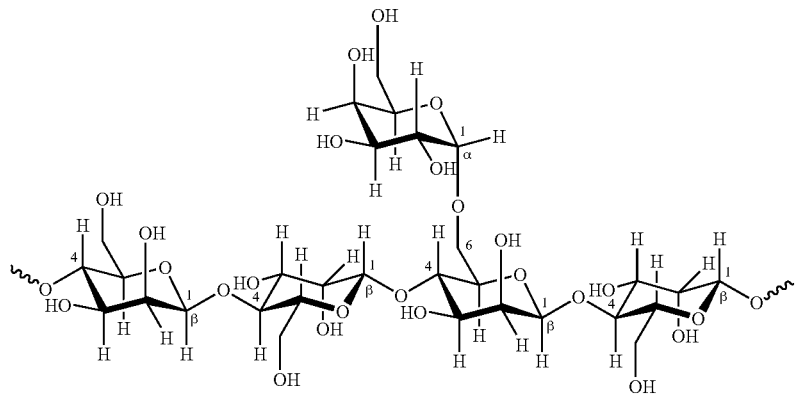

In one embodiment, the present invention relates to a formulation comprising about 0.001% to about 70% by weight of a stabilizing agent in an aqueous solution, or about 0.05% to about 25% by weight of a stabilizing agent, or about 0.1% to about 10% of a stabilizing agent. In another embodiment, the present invention relates to a formulation comprising about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or 1% by weight of a stabilizing agent in an aqueous solution. Preferably, the contrast agent is a formulation comprising about 0.01% to about 1.0% by weight.

5. Osmotic Agent

In one alternative embodiment, the contrast media of the present invention comprises an osmotic agent, such agents suitable for use herein including any compound that facilitates the transfer of fluid from the body into an anatomic segment and at least substantially inhibits the re-absorption of fluid in the anatomic segment by the body. It has been discovered that, when used in combination, the stabilizing agent and the osmotic agent act synergistically to form an improved formulation for use in a medical diagnostic procedure such as diagnostic imaging. It is believed that the osmotic agent facilitates the transfer of suitable amounts of fluid into an anatomic segment of interest and that stabilizing agent and osmotic agent cause sufficient amounts of fluid to be retained in the anatomic interest segment of interest. Thus, the anatomic segment is sufficiently expanded or distended for diagnostic imaging, such that when the anatomic segment is imaged, it appears sufficiently delineated on the diagnostic image obtained.

Osmotic agents suitable for use in the present invention include, but are not limited to, sugar-based compounds. Sugar-based compounds for use herein include, but are not limited to, monosaccharide, disaccharide and polysaccharides including sucrose, glucose, fructose, mannitol, mannose, galactose, aldohexose, altrose, talose, sorbitol, xylitol, lactose, nonionic seed polysaccharide, straight chain mannan grouping with branching on every mannose by one galactose unit, Beta-D-man, alpha-D-gal, D-glcA, D-galA, L-gul, beta-D-man, alpha-D-gal (4:1), D-glucuronic acid, D-galacturonic acid, and L-glucuronic acid. The chemical structure of a suitable polysaccharide is shown below.

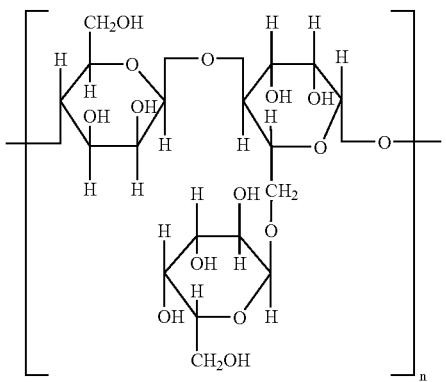

Preferably, the osmotic agent is sorbitol. It is believed that the underlying chemical structure of sorbitol prevents intestinal absorption of fluid. Thus, the inherent osmotic property of sorbitol leads to increased distention in an anatomic segment such as the GI tract, for example.

The formulation of the present invention may comprise about 0.005% to about 70% by weight of an osmotic agent, or about 0.1% to about 45% by weight of an osmotic agent, or about 1%, 2%, 3%, 4%, 5%, 6%, 7%, 8%, 9%, or 10% by weight of an osmotic agent. In one embodiment, the formulation comprises about 1% to about 4% by weight of an osmotic agent, preferably a polysaccharide, or even more preferably about 2% of sorbitol in an aqueous solution.

B. Exemplary Applications of the Contrast Media of the Present Invention

In one alternative embodiment, the formulations of the present invention are suitable for preparing an individual for a medical activity or for use simultaneously with such medical activity. Further, the contrast media of the present invention provide improved marking and organ differentiation during a medical activity. For example, in one embodiment, the image definition allows for the computer to define the differences between bowel wall, soft tissue, and bowel lumen distended with the contrast media of the present invention. In addition, the marking capabilities of the present contrast media allow for imaging of the vascular system at the same time.

In one embodiment, the contrast media of the present invention, when administered to an individual, will allow for differentiation between soft tissue and the bowel lumen distended by the low concentrations of contrast agent. The present contrast media will mark the lumen as its predecessor did in the older CT technology, but will enable differentiation between bowel marker, cystic lesions, lymph nodes and bowel lumen, for example, or any other anatomic segment with a different HV value. See Table 1.

TABLE 1

| Tissue | Standard value (HV) | Range (HV) | Fluid | Standard value (HV) |
|---|---|---|---|---|
| Bone (compact) | >250 | | Blood (coagulated) | 80 ± 10 |
| Bone (spongy) | 130 ± 100 | | Blood | 55 ± 5 |
| Thyroid | 70 ± 10 | | (venous whole blood) | |
| Liver | 65 ± 5 | 45-75 | Plasma | 27 ± 2 |
| Muscle | 45 ± 5 | 35-50 | Exudate (>30 g protein/l) | >18 ± 2 |
| Spleen | 45 ± 5 | 35-55 | Transudate | <18 ± 2 |
| Lymphoma | 45 ± 5 | 40-60 | (>30 g protein/l) | |
| Pancreas | 40 ± 10 | 25-55 | Ringer's solution | 12 ± 2 |
| Kidney | 30 ± 10 | 20-40 | | |
| Fatty tissue | −90 ± 10 | −80-(−110) | | |

An additional value of the present invention is also realized when vascular studies are performed. Thus, in an alternative embodiment, the present invention relates to a method of performing vascular studies on an individual using the contrast medias described herein. Such method comprising the step of distending the individual bowel by administering the contrast media of the present invention to the individual. Such method may also comprise the step of administering the present invention via IV to enhance the vascular system. By having the bowel distended and identified relative to the other abdominal structures for example, an abdomen may be scanned with a spiral/helical or multi-detector CT scanner, producing data sets that will construct a full volume rendered data set of the area scanned. In one embodiment, the formulations of the present invention could enable viewing of all organs and vessels independently or together as a complete data set. These formulations enable the lumen to be differentiated from the bowel wall while viewing the IV enhanced vascular system at the same time.

In one alternative embodiment, the present invention is directed to a method of performing CTA using the present formulations. Currently during CT Angiography (CTA) conventional oral contrast agents interfere with the image construction. CTA procedures are performed by injecting water soluble iodinated contrast agents into the vascular system. The contrast enhances the vascular structures of the abdomen. This process enhances the HV's of arterial and venous structures. The timing of the contrast injection and the timing of the scanning of the abdomen would enable the IV contrast in the arterial phase or the venous phase to be captured. During these procedures conventional oral contrast agents would interfere in the image.

The HV's of conventional oral contrast agents would compete with the IV contrast to create an image that would obscure vascular structures and would cause incomplete vascular structure image construction or masking bowel wall vascular or adjacent vascular structures. This occurs when the Maximum Intensity Pixel (MIP) technique is employed. Currently, specialized software will remove and reconstruct all of the MIP pixels from the abdomen data set. If IV contrast is used, the vessels of the abdomen become enhanced and these structures become intense pixels in the image. These pixels may provide a complete 3D image of the vascular structures of the abdomen. If conventional oral contrast is also used, the intensity of the pixels in the lumen of the GI tract competes with the vascular pixels. This causes loss of vascular structures since it is possible that some of the pixels in the lumen could be more intense than some smaller vessels and vessels of lower pixel intensity. The use of the current invention could allow for MIP studies and other display techniques to demonstrate vascular systems and mark the bowel during the same exam. Thus, the ability to see all abdominal and vascular structures would add to the overall understanding of disease in the abdomen and pelvis.

In another alternative embodiment, the present invention is directed to producing an HV value in the area below unenhanced bowel wall but higher than water. Previously, radiologists used water and fat containing products to achieve a negative HV value. In one embodiment, the formulations of the present invention provide a different approach by staying on the positive side of the HV's. With the present formulations, the lumen of the bowel can be marked, as barium sulfate and iodine have always done. But, with the present formulation, the marking stays below the HV's of the un-enhanced bowel wall. The low Hounsfield value of the present invention therefore becomes advantageous during any exam that requires enhancement of an atomic segment with IV contrast, such as the bowel wall. When using IV contrast, conventional bowel markers such as barium or iodine cannot be used because the density of these agents are too similar to the IV contrast and will hide anatomy or create artifacts when used together (i.e., oral barium or iodine with IV contrast).

In one alternative embodiment, the contrast media of the present invention is administered to an individual. In one embodiment, the HV values of the present formulation would fall below the range of the bowel wall enhanced with IV contrast, allowing it to mark the GI tract both before and after IV contrast enhancement. In one embodiment, the bowel wall will be enhanced with IV contrast raising the HV's to 60-90 or higher. When the present formulation is in the lumen, the difference in density from lumen (22 HVs) to the enhanced bowel wall (90+ HVs) would be clear. Bowel wall is in the 45 HV range (unenhanced) and the bowel wall can exceed 100 HVs with IV contrast. Also, the bowel may be marked for purposes of diagnosing the GI tract and other organs and vascular system simultaneously. This has not been previously accomplished with a positive contrast agent in the GI tract. Therefore, in one embodiment, the present invention is directed to a method of marking the bowel using the present contrast media, enabling the bowel to be differentiated from surrounding structures and allow for additional diagnostic evaluations at the same time, with or without enhancing other atomic segments using IV contrast. In one alternative embodiment, the above procedure may be carried out using spiral/helical or MSMD CT scanners.

In another alternative embodiment, the present contrast media may comprise modified charges on the contrast agent, e.g. barium particles to attract them to the bowel wall leaving the lumen distended with lower concentrations of the contrast agent in the lumen. Leaving a slightly higher coating film containing higher concentrations of the active ingredient on the mucosal surface could improve image quality.

In one alternative embodiment, the present invention relates to a method of reducing the signal/noise ratio in MR. The method comprising the step of administering the present contrast media to the individual prior to or during an MR procedure. In one embodiment, the present contrast media would create a darker (i.e., void, no signal or low signal) image with or without the addition of such additives as bentonite, for example. This additional contrast difference between the lumen and the unenhanced bowel wall could allow one to mark the GI tract before or after IV contrast enhancement. The bowel wall will enhance with IV contrast raising its signal/noise ratio. In one embodiment, this causes the wall to become bright. When using MR and the present formulation with or without the addition of bentonite in the lumen (for example), the difference in contrast from lumen (darker, void, no signal or low signal) to the enhanced bowel wall (which appears bright, white with increase signal/noise ratio) would be clear. Also, the bowel may be marked for purposes of diagnosing the GI tract and other organs and vascular system simultaneously.

In one embodiment, the formulations of the present invention may be administered to an individual prior to the individual undergoing an image guided biopsy of the GI tract, or any adjacent organs such as liver, spleen, pancreas, kidney, lymph nodes and the like. The added value of a clear visualization of the bowel wall and lumen may allow for a better understanding of bowel location for more precise placement of the biopsy needle. This would offer the opportunity to avoid puncture of bowel loops that would otherwise not be easily visualized when taking a biopsy of tissue located in the abdomen or pelvis.

In another embodiment, the formulations of the present invention may be used to stabilize the GI tract of an individual in order to obtain a diagnostic image of the vasculature system or the lymph nodes or other anatomical structures. In addition, the ability to decrease movement of the GI tract during PET or CT-PET leads to improvement in co-registration of CT and PET data sets. Thus, in one embodiment, the present invention relates to a method of stabilizing the GI tract of an individual during a surgical or diagnostic procedure, for example. Such method comprising the step of: (1) administering the present contrast media to the individual prior to or during the diagnostic or medical procedure for purposes of stabilizing an individual's GI tract; and (2) conducting the diagnostic or medical procedure.

In another embodiment, the present invention further relates to formulations for delineating the lumen or wall of an anatomic segment of the GI tract on a diagnostic image. The diagnostic image being a two- or three-dimensional or volumetric or a surface rendered image of the anatomic segment, for example. Thus, in one embodiment, the present invention relates to a method of delineating the lumen or wall of an anatomic segment of an individual's GI tract. Such method comprising the step of: (1) administering the present contrast media to the individual prior to or during the diagnostic procedure; (2) conducting the diagnostic procedure; and (3) generating the image of the delineated lumen or wall of an anatomic segment.

In another alternative embodiment, the formulations of the present invention represent an improvement over conventional contrast agents or formulations for distending, delineating or marking an anatomical segment of the GI tract, or any other anatomic segment. For example, the conventional technique of distending the small bowel is by administering a methylcellulose-water solution via intubation, an unpleasant invasive procedure. The present formulations, however, may be administered orally. Therefore, the formulations of the present invention are non-invasive, and also may maintain the integrity of diagnostic imaging as a non-invasive technique. Also, when administered orally, the present formulations increase patient comfort and compliance as compared to conventional contrast agents.

The low HV value of the present contrast media allows for universal acceptance in CT, CT angiography, CT-PET, PET, MR, Fluoroscopy, and US. For example, the universal use of the contrast agent may allow a patient to be moved from one imaging modality to another without delay between procedure. In one embodiment, the multi-modality use of the contrast allows an individual having the present invention in the GI tract to be imaged by one imaging modalities and taken to another for additional imaging. Here, the patient need only be prepped once, and can still use different imaging modalities by administering the present media to that individual prior to or during an imaging procedure.

In one embodiment, the present invention relates to a method of imaging the small intestine of an individual comprising administering the formulations disclosed herein and using MR, CT, US, PET or CT-PET to obtain a visible image of the small intestine. Other anatomic segments suitable for use herein include, but are not limited to, esophagus, the stomach and GI tract, including the duodenum, jejunum, ileum, appendix, colon, large intestine, cecum, ascending bowel, hepatic flexure, transverse colon, splenic flexure, descending colon, sigmoid, rectum, pancreas, gall bladder, and appendix. Additional adjacent normal and pathologic structures such as spleen, liver, lymph nodes, vasculature, abcesses and the like can be imaged.

In an alternative embodiment, the present invention relates to a method of diagnosing a disease in an individual comprising administering to the patient the formulations of the present invention. In one embodiment, the method further comprises obtaining an image of the anatomic segment and using said image to diagnose said disease. In an alternative embodiment, the present invention relates to a method of diagnosing a disease in a patient comprising the steps of: (1) administering to an individual a formulation comprising the present invention; (2) obtaining an image of the anatomic segment using MR, CT, CT-PET, PET, (3) using said image to diagnose or assist in diagnosing a disease, and optionally (4) obtaining an image using a positive IV agent to enhance bowel wall, allowing the present invention to fill, mark, and distend the bowel, creating a double contrast effect with all previously mentioned routes of administration.

In another alternative embodiment, the present invention relates to a method for diagnosing a disease including, but not limited to, diseases of the GI tract, ulcerations, lesions, strictures intermittent or fixed and tumors of the GI tract or stomach, Inflammatory Bowel Disease, Crohn's Disease, ulcerative colitis, Irritable Bowel Syndrome, and cancer including, but not limited to, cancer of the small bowel, anal cancer, stomach cancer, colon cancer, liver cancer and pancreatic cancer, abscesses, ulcers and disorders of the spleen, liver, lymph nodes and vasculature.

In yet another embodiment, the present invention relates to a method of enhancing image quality during interventional procedures requiring placement of vascular stents or interlumenal stents of the GI tract, and other common hepatobiliary, pancreatic and renal interventional procedures. In one embodiment, such method comprises the steps of: (1) administering to an individual the present contrast media; (2) conducting one or more procedures requiring placement of vascular stents or interlumenal stents of the GI tract; and (3) generating a diagnostic image during said procedures. Preferably, the diagnostic image is a two- or three-dimensional image, volumetric and surface rendered or a combination of the two created using MR, CT or CT-PET data.

In another embodiment, the present invention relates to a method of improving the accuracy of knowing the exact location of distended bowel prior to intervention, surgery, radiation therapy, vascular or gastrointestinal stent placement, enteroscopy, laparoscopy etc.

In one embodiment, such method comprises the steps of: (1) administering to an individual the present contrast media; (2) generating a diagnostic image to identify the location of a distended bowel prior to one or more procedures, including but not limited to, intervention, surgery, radiation therapy, vascular or gastrointestinal stent placement, enteroscopy, or laparoscopy; and (3) conducting such procedures.

The present formulations may be administered to an individual to mark the GI tract during therapeutic treatment or planning for such treatment. Here, ulcerations, lesions or tumors of the GI tract, GI tract bleeding, Inflammatory Bowel Disease, Crohn's Disease, ulcerative colitis or Irritable Bowel Syndrome can be imaged by utilizing one or more of the imaging modalities discussed herein.

The present invention may be used as a small bowel contrast marker while performing CT Colonography. The purpose is to create mechanical resistance by filling the lumen with contrast that can impede the likelihood of having small bowel reflux of CO2 or room air when administered during CT Colonography. This technique may allow one to obtain high quality small bowel examination at the same time and with same exposure during either a CT or MR Colonography. Additionally, the concept may be able to impede reflux of CO2 or room air into small bowel, optimizing distention of the colon. Thus, the present invention is directed to marking the small bowel while performing CT colonography, including the step of administering the present contrast media to an individual prior to or during a CT colonography procedure, and then generating an image of the anatomic segment of interest.

The contrast media of the present invention comprise lower concentrations of contrast agent than those of conventional media. Lower concentrations of the "active ingredient" in contrast agents provides several advantages, most notably, potentially reducing risk of allergic or other adverse reactions.

VI. EXAMPLES

The following examples are included for illustrative purposes only and are not intended to limit the scope of the invention to any particular step or ingredient, for example.

Example 1

Formulations A through D were prepared as follows: Xanthan Gum in powdered form was added in water. The temperature of the suspension was maintained at 60-65° C. throughout manufacturing. Other ingredients were added: simethicone-water premix; preservatives: potassium sorbate, sodium benzoate and benzoic acid; pH adjuster: sodium citrate and citric acid; dispersion of barium sulfate USP; addition of the rest of the ingredients in the following order: sorbitol 70% solution, saccharin sodium, flavours; Qs to 100% volume with purified water.

Differences between each formulation include (1) the equipment used in the manufacturing process and (2) the concentration of ingredients. For example, Formulations A and B were laboratory batches of 7000 ml. These batches were manufactured in a glass beaker. The formulation was prepared under lightning agitation. The product's manufacturing temperature was monitored manually and the temperature was maintained with a water bath at 60-65° C.

Formulations C and D were manufactured in a Hamilton kettle, which is made of stainless steel and has a capacity of 200 gallons. A Quadro Ytron mixer, a side sweep and auxiliary mixers made the Hamilton kettle's agitation. The agitation speed of each mixer was variable and controlled with an adjustable speed drive. The control of the temperature, between 60-65° C., was done manually by controlling the flow of water/steam flowing into the cooling jacket. The manufacturing process of formulations C and D used the Quadro turbine and side sweep agitation from the beginning until the end. The auxiliary agitation started at the barium sulfate addition and finished after the second addition of the xanthan powder.

Other differences between formulations A to D are the concentrations of barium sulfate, the xanthan gum and sorbitol. Formulation A was manufactured without barium sulfate while batch formulation B was made with 0.1 w/v % of barium sulfate. Formulations C and D were made with 0.05 w/v % of barium sulfate.

TABLE 2

| Ingredient | A Formulation, % w/v | B Formulation, % w/v | C Formulation, % w/v | D Formulation, % w/v | Function of Ingredient |
|---|---|---|---|---|---|
| Barium Sulfate USP, EP | 0.0000 | 0.1000 | 0.0500 | 0.0500 | Radiographic Contrast Agent |
| Xanthan Gum, NF | 0.5226 | 0.1828 | 0.5226 | 0.1830 | Suspension stabilizer |
| Sorbitol solution 70%, USP | 3.7616 | 2.8571 | 2.0000 | 2.0000 | Osmoregulator |
| Viscosity | 719 cps | 128 cps | 860 cps | 140 cps | |
| Density | 1.0100 g/ml | 1.0100 g/ml | 1.006 g/ml | 1.005 ag/ml | |
| pH | 4.95 | 4.95 | 5 | 5 | |
| Potassium Sorbate, NF | | 0.2090 | | | Preservative |
| Sodium Benzoate, NF | | 0.0433 | | | |
| Benzoic Acid, USP/BP | | 0.0696 | | | |
| Simethicone Emulsion, USP | | 0.5226 | | | Defoamer |
| Citric Acid, USP | | 0.0028 | | | pH adjuster |
| Sodium Citrate, USP | | 0.0076 | | | |
| Flavors & artificial sweetener | | 0.4309 | | | Flavorings |
| Purified water USP | | q.s. to 100% volume | | | Diluent |

Formulations A and C were made with the regular concentration of xanthan gum found into the current banana smoothie formula (0.5226 w/v %) while formulations B and D were manufactured with 35% of the regular concentration of xanthan gum found in the current banana smoothie formula (0.1830 w/v %). The xanthan gum concentration difference gives high and low viscosities solutions of approx. 720 and 130 cps. Formulation A was manufactured with 3.7616 w/v % of sorbitol solution 70% which is identical to the concentration found into the banana smoothie formulation. Formulation B was made with 2.8571 w/v % of sorbitol solution 70%. This concentration represents 2 w/v % @100% of sorbitol. Formulation B was manufactured with 2 w/v % of sorbitol solution 70%.

Example 2

A contrast media having the following formulation was prepared in accordance with the steps described in Example 1.

TABLE 3

| | Description | % Quantity |
|---|---|---|
| 1 | PURIFIED WATER USP | 66.6700 |
| 2 | XANTHAN GUM NF/EP/BP | 0.0914 |
| 3 | SIMETHICONE EMULSION 30% USP | 0.0673 |
| 4 | PURIFIED WATER USP | 0.0716 |
| 5 | POTASSIUM SORBATE NF | 0.2090 |
| 6 | SODIUM BENZOATE NF | 0.0433 |
| 7 | BENZOIC ACID USP/BP | 0.0696 |
| 8 | SOD CITRATE DIHYD USP/EURPH | 0.0076 |
| 9 | CITRIC ACID ANH (PWD) USP | 0.0028 |
| 10 | PURIFIED WATER USP | 0.5556 |
| 11 | BARIUM SULFATE HN USP | 0.1000 |
| 12 | XANTHAN GUM NF/EP/BP | 0.0914 |
| 13 | SIMETHICONE EMULSION 30% $ USP | 0.4553 |
| 14 | PURIFIED WATER USP | 0.4840 |
| 15 | SORBITOL SOL'N 70% USP | 2.8571 |
| 16 | SODIUM SACCHARIN USP/EP/BP | 0.0109 |
| 17 | SAV BLEUET W390007F MFR | 0.1500 |
| 18 | PURIFIED WATER USP | QS |

Example 3

Using a Seimens 4 channel scanner, the HV values of the present contrast media were determined. The formulas evaluated were:
1. 0.05% w/v barium sulfate, 860 CPS, 2% sorbitol (Formulation C)
2. 0.05% w/v barium sulfate, 140 cps, 2% sorbitol (Formulation D)
3. No barium sulfate, 719 cps, 2% sorbitol (Formulation B)
4. 0.1% w/v barium sulfate, 128 cps, 2% sorbitol (Formulation A).

Figure 5A:
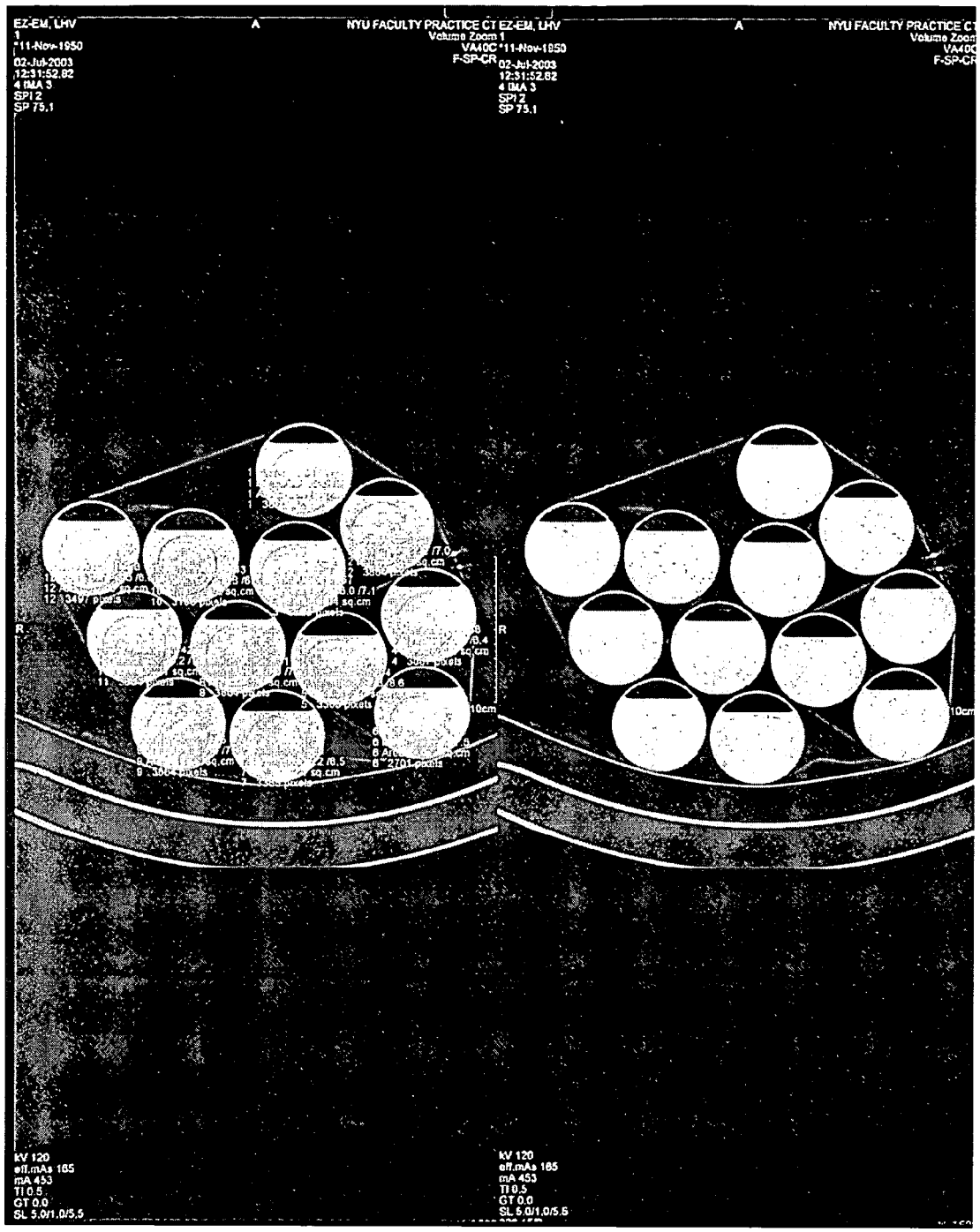
FIG. 5 shows CT images of the present media in an HDPE container.
Figure 5B:
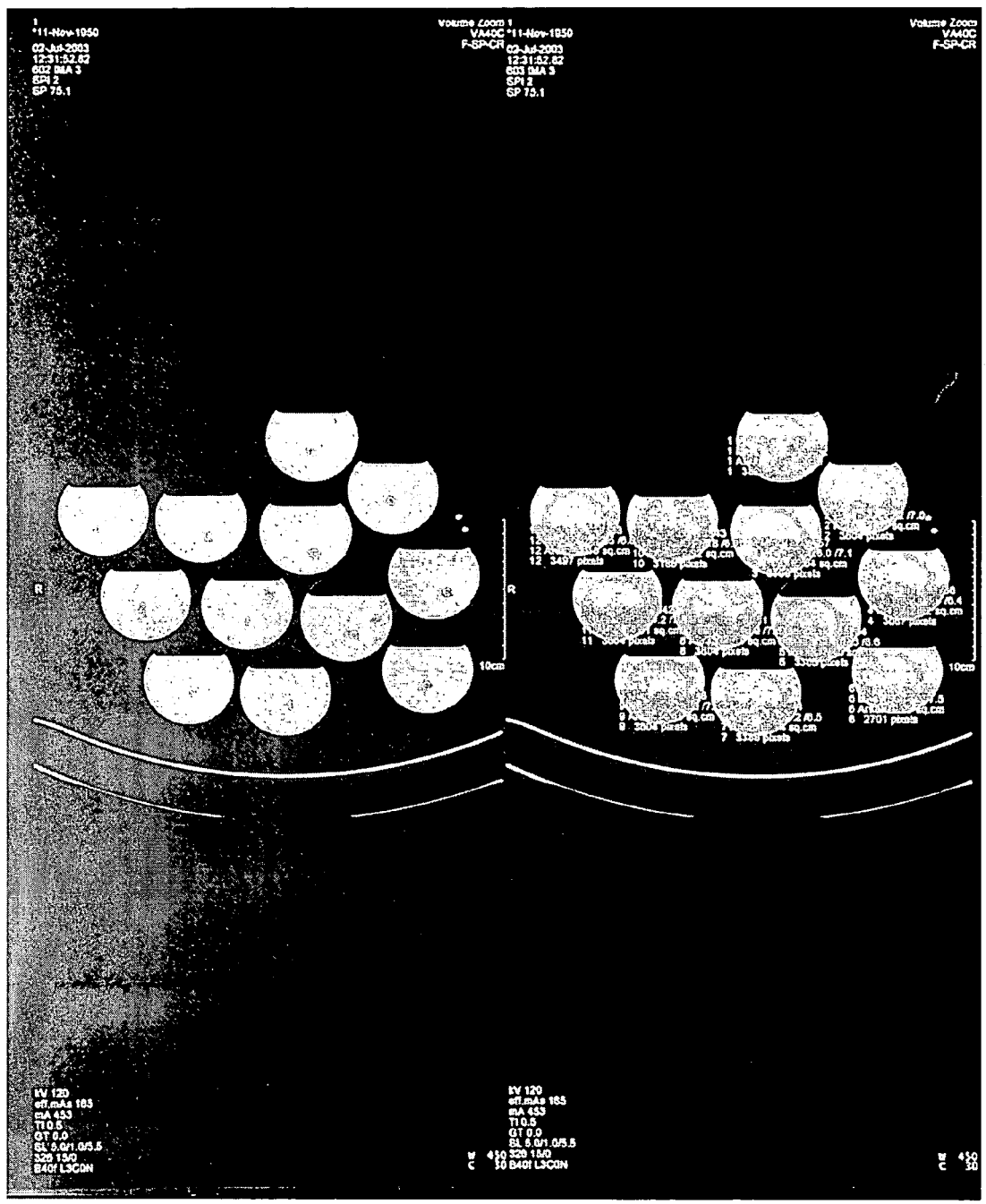

The constrast media was placed in a 500 ml HDPE container and then placed in the CT scanner for measurement. The containers were arranged in a manner shown in FIG. 5. Several spiral slices were made through the HDPE containers to establish the formulations' HV's. The results were as follows:
1. 0.05% w/v barium sulfate, 860 CPS, 2% sorbitol (Formulation C)
   1. Mean/SD 16.9/7.8 HV's
   2. Mean/SD 16.0/7.8 HV's
   3. Mean/SD 17.2/6.5 HV's
2. 0.05% w/v barium sulfate, 140 cps, 2% sorbitol (Formulation D)
   1. Mean/SD 12.5/6.8 HV's
   2. Mean/SD 14.8/6.8 HV's
   3. Mean/SD 14.2/7.9 HV's
3. No barium sulfate, 719 cps, 2% sorbitol (Formulation B)
   1. Mean/SD 12.3/8.6 HV's
   2. Mean/SD 6.9/6.4 HV's
   3. Mean/SD 7.2/7.5 HV's
4. 0.1% w/v barium sulfate, 128 cps, 2% sorbitol (Formulation A)
   1. Mean/SD 23.5 6.2 HV's
   2. Mean/SD 22.2/7.0 HV's
   3. Mean/SD 26.0/7.1 HV's
5. The ROI on an area of the colon with barium (E-Z-EM's banana smoothie) was Mean/SD 313.2/13.8 HV's.

This test demonstrated the 0.1% w/v barium sulfate concentration was preferred because it had a clear difference in HV's from the base and 0.5% BaSO4 formulations. The range of values for the 0.1% formula at a low viscosity was 23.9 HV's, which matched the prefered target range of 20 to 30 HV's.

The 0.1% w/v BaSO4 enabled marking of the lumen/bowel wall in Multi-detector Scanners while preserving the contrast differentiation of un-enhanced bowel lumen. When abdominal, pelvic studies were conducted without IV contrast. The 0.1% w/v BaSO4 will mark the bowel while offering an improved image of the GI tract itself. The contrast (difference) between the bowel wall enhanced by IV contrast and this contrast media will become more pronounced. The bowel wall with contrast on board will demonstrate an increase in HV's (+100 HV's) due to the increased density of the IV contrast.

Example 4

Clinical evaluations of the formulations of the present invention are discussed below. The HV for each contrast media is described in Example 3. Each trial showed satisfactory bowel lumen distention, uniform distribution, and good patient acceptance.

MR

Formulation D was administered to a healthy volunteer. The volunteer consumed 1.35 liters or three (3) bottles (450 ml/dose) of the contrast media within 45 minutes of an abdominal examination. The contrast media contained banana flavoring. The abdominal examination was performed using MR as the diagnostic imaging modality. The MR images were generated using an MR scanner by Siemens (Sonata).

Figure 3:
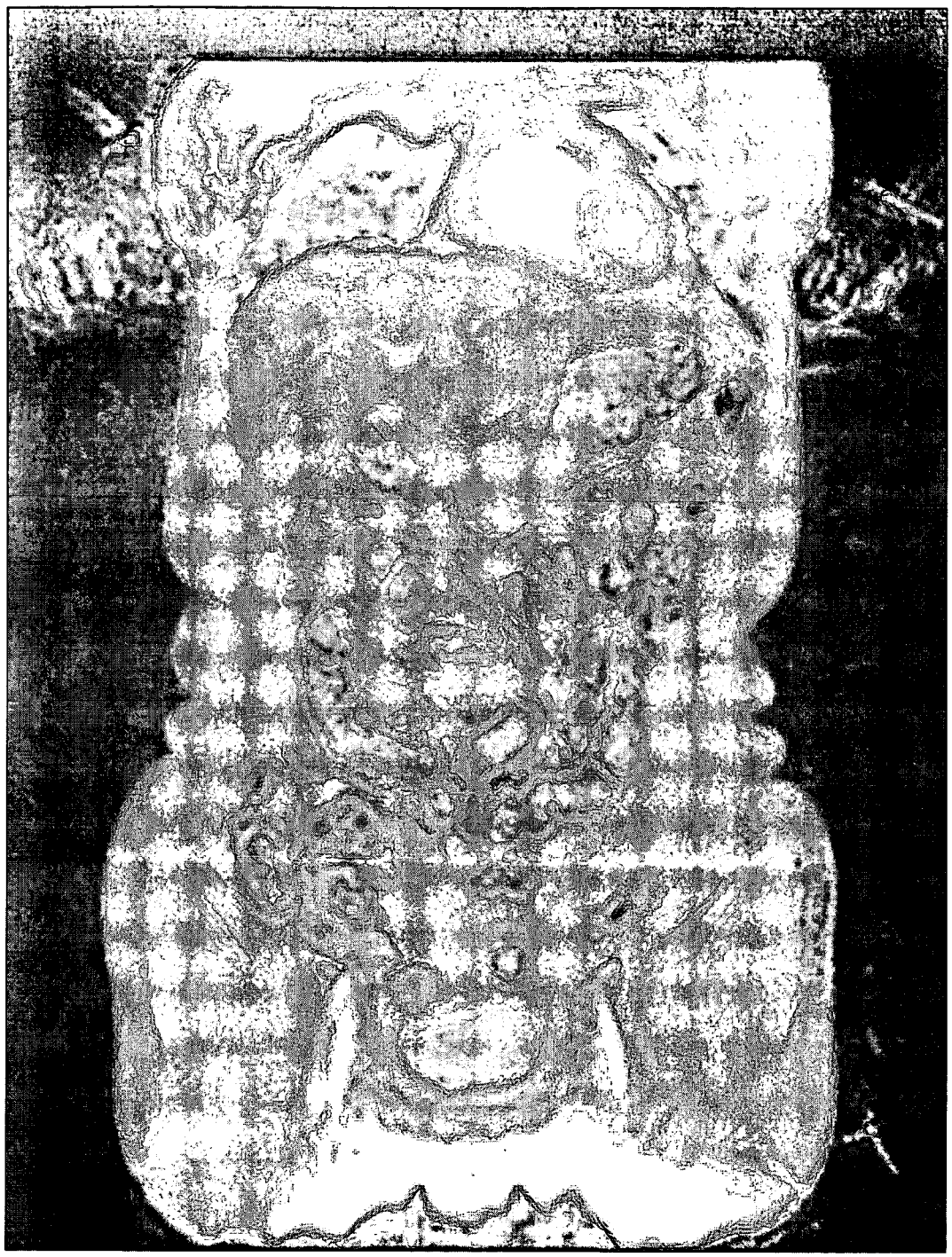
FIG. 3 shows a CT image of an abdomen of an individual administered the present invention.
Figure 4:
FIG. 4 shows an MR image of an abdomen of an individual administered the present invention.

The patient expressed no complaints about the contrast media's formula, flavor, viscosity or volume. The patient experienced no adverse events. The patient was placed in the prone position while the abdomen was scanned. Images obtained from the MR scan are shown in FIGS. 3 and 4. The MR images show total abdomen and pelvis, with stomach and small bowel distended and/or marked by the contrast media. These images confirm that the contrast media marked the GI track, allowing for diagnostic evaluation of the intestine and surrounding tissue in the abdomen and pelvis. In FIG. 3, this image of the abdomen demonstrate the present media's ability to mark and distend the bowel. Here, the marker is dark and the soft tissue of the GI tract is bright. In FIG. 4, this image of the abdomen demonstrates the benefits of marking and distending the stomach and small bowel in the contrast with the signal of bowel wall. Here, the marker is bright and the bowel wall is dark. Additionally, bowel distention was uniform and adequate, and the contrast was consistent though out the length of the small bowel.

Figure 2:
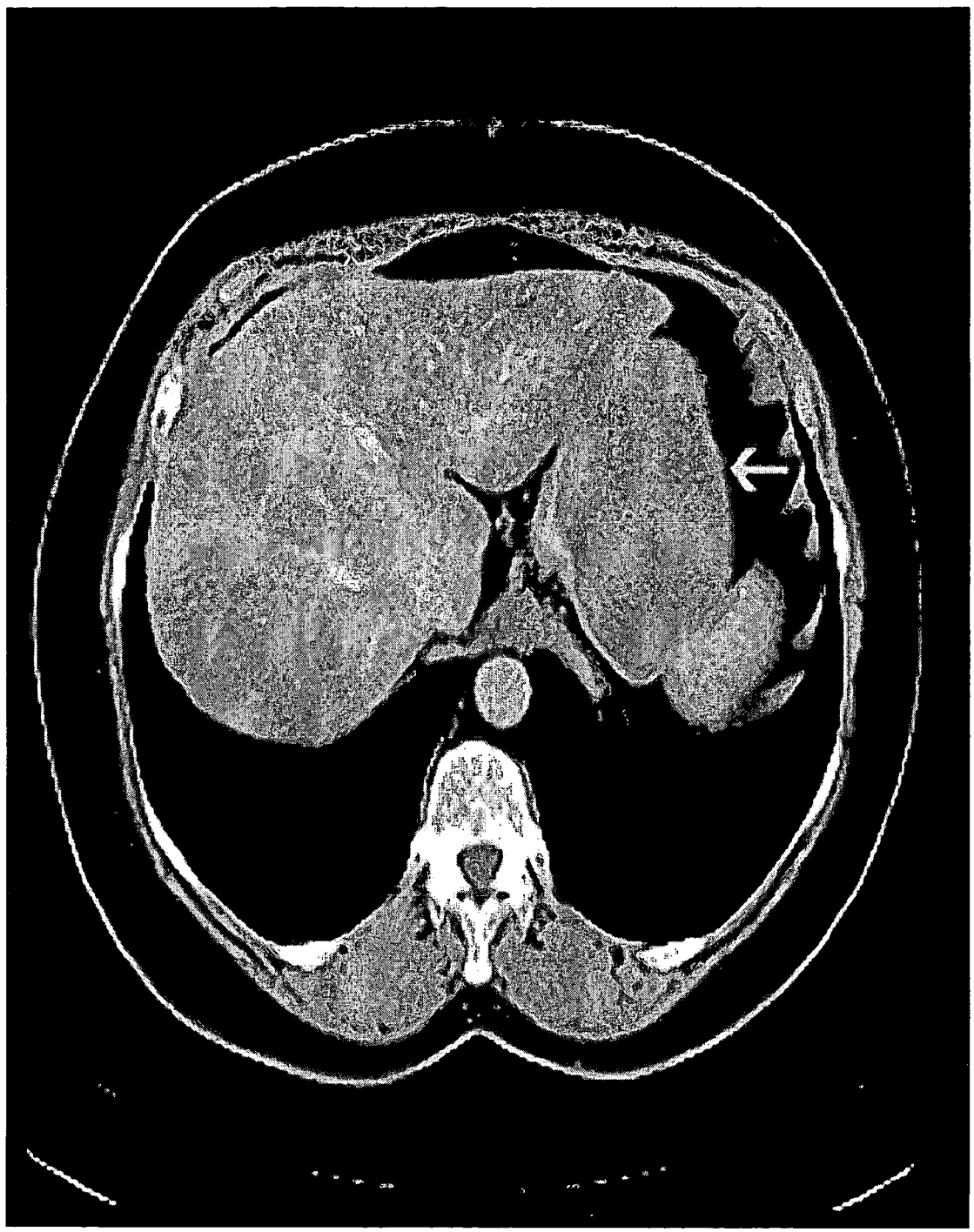
FIG. 2 shows a CT image of an abdomen of an individual administered the present invent invention.

Further, it was observed that several hundred ml of the contrast media remained in the stomach during the exam. In FIGS. 1 and 2, the signal intensity (signal/noise ratio) was satisfactory in all sequences used, and it was consistent through out the small bowel lumen.

Example 5

CT

Formulation C was administered to a patient previously scheduled for an abdominal CT. The patient consumed 2 doses (450 ml/dose, total volume 900 ml) within 45 minutes. Immediately thereafter, the patient's abdomen was scanned in the prone position. CT images were generated using a 16 slice CT scanner by Siemens (Sensation 16). The CT image (FIGS. 1 and 2) shows gastric filling with clear differentiation between contrast and stomach wall (FIG. 2, Arrow). In FIG. 1, contrast is found in the body of the stomach and proximal small bowel. It also shows small bowel filling and distention (FIG. 1, Arrow). Further, the images (FIG. 2) show that the contrast media satisfactory filled and distended the stomach. The contrast filled lumen will clearly differentiate itself from the soft tissue density of the lumen wall due to its low HV. The patient experienced no adverse events.

Prior to the CT exam, the patient expressed no complaints about the contrast media's formula, flavor, viscosity or volume.

Throughout the description, where the present invention is described as having, including, or comprising specific components, or where processes are described as having, including, or comprising specific process steps, it is contemplated that the present invention also consists essentially of, or consists of, the recited components or processing steps. Further, it should be understood that the order of steps or order for performing certain actions are immaterial so long as the invention remains operable. Moreover, two or more steps or actions may be conducted simultaneously so long as the invention remains operable. Also, one or more steps or elements may be omitted from the claimed invention, or the invention described herein suitably may be practiced in the absence of any component or step which is not specifically disclosed herein, so long as the invention remains operable.

Further, the present invention may be embodied in other specific forms without departing from the spirit or essential characteristics thereof. The foregoing embodiments are therefore to be considered illustrative rather than limiting the invention described herein. The content of each patent and non-patent document referred to herein is expressly incorporated herein by reference in its entirety.

I claim:

1. A contrast media for use in imaging an individual's anatomic segment comprising: a contrast agent in an aqueous suspension; wherein the contrast agent comprises about 0.01% w/v to about 0.2% w/v of a barium-based compound and the contrast media having a Hounsfield value from about 0 to about 50, and said contrast media further comprising 0.005% to about 70% by weight of a sugar selected from the group consisting of sorbitol, mannitol and xylitol.

2. The contrast media of claim 1, wherein the Hounsfield value is from about 5 to about 50.

3. The contrast media of claim 1, wherein the Hounsfield value is about 5 to about 45.

4. The contrast media of claim 1, wherein the Hounsfield value is about 15 to about 35.

5. The contrast media of claim 1, wherein the Hounsfield value is about 20 to about 30.

6. The contrast media of claim 1, wherein the concentration of the contrast agent is about 0.1% w/v to about 0.2% w/v.

7. The contrast media of claim 1, wherein the concentration of the contrast agent is selected from the group consisting essential of 0.02%, 0.03%, 0.04%, 0.06%, 0.07%, 0.08%, 0.09%, 0.11%, 0.15%, 0.2%, or 0.25% w/v.

8. The contrast media of claim 1, wherein the barium-based compound is barium sulfate.

9. The contrast media of claim 1, further comprising a stabilizing agent.

10. The contrast media of claim 1, further comprising about 0.005% w/v to about 40% w/v of a stabilizing agent.

11. The contrast media of claim 9, wherein the stabilizing agent comprises about 0.05% w/v to about 10% w/v xanthan gum.

12. The contrast media of claim 1, wherein the concentration of the sugar is about 0.005% w/v to about 60% w/v.

13. A contrast media for use in imaging an individual's anatomic segment comprising from about 0.01% to about 0.2% w/v of a barium-based compound; about 0.05% w/v to about 25% w/v of a stabilizing agent and about 0.005% w/v to about 70% w/v of a sugar selected from the group consisting of sorbitol, mannitol and xylitol.

14. The contrast media of claim 13, wherein the stabilizing agent comprises xanthan gum and the sugar comprises sorbitol.

15. The contrast media of claim 13, comprising about 0.1% w/v to about 0.2% w/v barium-based compound; about 0.05% w/v to about 1% w/v xanthan gum and about 0.05% w/v to about 5% w/v sorbitol.

16. The contrast media of claim 13, comprising about 0.1% w/v to about 10% w/v of a stabilizing agent.

17. The contrast media of claim 13, comprising about 0.1% w/v to about 45% of a sugar selected from the group consisting of sorbitol, mannitol and xylitol.

18. The contrast media of claim 13, wherein the sugar is sorbitol.

19. The contrast media of claim 13, comprising about 0.01% w/v to about 0.2% w/v barium-based compound; about 0.1% w/v to about 10% w/v xanthan gum and about 1% w/v to about 15% w/v sorbitol.

20. A method for imaging an anatomic segment, tissue or organ inside an individual's body comprising: (a) administering a contrast media to an individual; said contrast media comprising about 0.01% w/v to about 0.2% w/v barium-based contrast agent and a sugar selected from the group consisting of sorbitol, mannitol and xylitol in an aqueous suspension, said contrast media having a Hounsfield value from about 0 to about 50 ; and (b) performing a diagnostic procedure on the individual during or after administering the contrast media to the individual.

21. The method of claim 20, wherein the contrast media has a Hounsfield value from about 5 to about 50.

22. The method of claim 20, wherein the Hounsfield value is about 10 to about 40.

23. The method of claim 20, wherein the Hounsfield value is about 5 to about 45.

24. The method of claim 20, wherein the Hounsfield value is about 15 to about 35.

25. The method of claim 20, wherein the Hounsfield value is about 20 to abut 30.

26. The method of claim 20, wherein the concentration of the contrast agent is from about 0.1% w/v to about 0.2% w/v.

27. The method of claim 20, wherein the concentration of the contrast agent is 0.1% w/v or 0.2% w/v.

28. A method of imaging an anatomic segment of an individual comprising the steps of: (a) administering a contrast media comprising about 0.01% w/v to about 0.2% w/v of a barium-based contrast agent and a sugar selected from the group consisting of sorbitol, mannitol and xylitol in an aqueous suspension; said contrast media having a Hounsfield value from about 0 to about 50; (b) conducting an imaging procedure to obtain the image of the individual's anatomic segment during or after administering the contrast media to the individual; and (c) generating the image of the anatomic segment.

29. The method of claim 28, wherein at least a portion of the gastrointestinal tract is imaged.

30. The method of claim 28, wherein the small intestine is imaged.

31. The method of claim 28, wherein the colon is imaged.

32. The method of claim 28, wherein the pancreas is imaged.

33. The method of claim 28, wherein the duodenum is imaged.

34. The method of claim 28, wherein the cecum is imaged.

35. The method of claim 28, wherein the bowel is imaged.

36. The method of claim 28, wherein the large intestine is imaged.

37. The method of claim 28, wherein the jejunum is imaged.

38. The method of claim 28, wherein the ileum is imaged.

39. The method of claim 28, wherein the appendix is imaged.

40. The method of claim 28, wherein the pancreas is imaged.

41. The method of claim 28, wherein the duodenum is imaged.

42. The method of claim 28, wherein the sigmoid is imaged.

43. The method of claim 28, wherein the rectum is imaged.

44. The method of claim 28, wherein the stomach is imaged.

45. A method of diagnosing a disease in an individual comprising: (a) administering to said individual a contrast media comprising a contrast agent wherein said contrast agent comprises about 0.01% w/v to about 0.2% w/v of a barium-based compound and a sugar selected from the group consisting of sorbitol, mannitol and xylitol in an aqueous suspension; said contrast media having a Hounsfield value from about 0 to about 50; (2) conducting an imaging procedure to obtain the image of an individual's anatomic segment; (3) generating the image of the anatomic segment; and (4) evaluating the images to diagnose the presence of the disease.

46. The method of claim 45, wherein said disease is selected from the group consisting of ulcerations, lesions and tumors.

47. The method of claim 45, wherein said disease is cancer.

48. The method of claim 45, wherein said disease is inflammatory bowel disease, Crohn's Disease, ulcerative colitis or irritable bowel syndrome.

49. The method of claim 45, wherein said disease is a disease of the pancreas, spleen, liver or gall bladder.

50. The method of claim 45, wherein said disease is a disease of the lymph nodes.

51. The method of claim 45, wherein said disease is a disease of the vascular system.

52. A method of delineating the lumen of an anatomic segment of an individual for a diagnostic procedure, said method comprising the steps of: (a) providing an aqueous suspension comprising about 0.01% w/v to about 0.2% w/v of a barium-based compound and a sugar selected from the group consisting essentially of sorbitol, mannitol and xylitol into the lumen of the individual's anatomic segment to facilitate delineation of the anatomic segment; said contrast media having a Houndsfield value from about 0 to about 50.

53. A method of distending an anatomic segment of an individual for a medical or diagnostic procedure comprising the steps of: (a) providing an aqueous suspension comprising about 0.01% w/v to about 0.2% w/v of a barium-based compound and a sugar selected from the group consisting essentially of sorbitol, mannitol and xylitol into the lumen of the individual's anatomic segment to facilitate distention of the anatomic segment; said contrast media having a Houndsfield value from about 0 to about 50.

54. The method of claims 52 or 53, wherein said anatomic segment is the gastrointestinal tract.

55. The method of claims 52 or 53, wherein said anatomic segment is the small intestine.

56. The method of claims 52 or 53, wherein said anatomic segment is the large intestine.

57. The method of claims 52 or 53, wherein said anatomic segment is the colon.

58. The method of claims 52 or 53, wherein said anatomic segment is the bowel.

59. The method of claims 53 or 53, wherein, said contrast media has a Hounsfield value from about 0 to about 50.

60. The method of claims 52 or 53, wherein the Hounsfield value is about 0 to about 50.

61. The method of claims 43 or 53, wherein the Hounsfield value is about 5 to about 45.

62. The method of claims 50 or 53, wherein the Hounsfield value is about 15 to about 35.

63. The method of claims 52 or 53, wherein the Hounsfield value is about 20 to about 30.

64. The method of claims 52 or 53, wherein the concentration of the concentration is from about 0.1% w/v to about 0.2% w/v.

65. The method of claims 52 or 53, wherein the concentration of the contrast agent is selected from the group consisting essentially of the contrast media of claim 1, wherein the concentration of the contrast agent is selected from the group consisting essential of 0.02%, 0.03%, 0.04%, 0.06%, 0.07%, 0.08%, 0.09%, 0.11%, 0.15%, or 0.2% w/v.

* * * * *

UNITED STATES PATENT AND TRADEMARK OFFICE
CERTIFICATE OF CORRECTION

PATENT NO. : 7,498,018 B2  Page 1 of 1
APPLICATION NO. : 10/679052
DATED : March 3, 2009
INVENTOR(S) : Williams et al.

It is certified that error appears in the above-identified patent and that said Letters Patent is hereby corrected as shown below:

Title Page

(75) Inventor: should read

--Archie B. Williams, III, New Smyrna Beach, FL (US)

Michael A. David, Sharon, MA (US)

1Howard S. Stern, Deceased--

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,498,018 B2 Page 1 of 1
APPLICATION NO. : 10/679052
DATED : March 3, 2009
INVENTOR(S) : Williams et al.

It is certified that error appears in the above-identified patent and that said Letters Patent is hereby corrected as shown below:

Title Page

(75) Inventor: should read

--Archie B. Williams, III, New Smyrna Beach, FL (US)

Michael A. Davis, Sharon, MA (US)

Howard S. Stern, Deceased--

This certificate supersedes the Certificate of Correction issued March 30, 2010.

Signed and Sealed this

Fourth Day of May, 2010

David J. Kappos
*Director of the United States Patent and Trademark Office*